United States Patent
Shimose et al.

(10) Patent No.: US 7,094,870 B2
(45) Date of Patent: Aug. 22, 2006

(54) CRYSTALS OF OXIDIZED GLUTATHIONE AND PROCESS FOR PRODUCING THE SAME

(75) Inventors: Tsuyoshi Shimose, Shunan (JP); Hideki Murata, Hofu (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 23 days.

(21) Appl. No.: 10/492,127

(22) PCT Filed: Oct. 25, 2002

(86) PCT No.: PCT/JP02/11110

§ 371 (c)(1),
(2), (4) Date: Apr. 7, 2004

(87) PCT Pub. No.: WO03/035674

PCT Pub. Date: May 1, 2003

(65) Prior Publication Data

US 2004/0250751 A1    Dec. 16, 2004

(30) Foreign Application Priority Data

Oct. 25, 2001    (JP) .............................. 2001-327295

(51) Int. Cl.
*C07K 5/037*    (2006.01)
(52) U.S. Cl. ...................... 530/332; 530/344
(58) Field of Classification Search .................. 530/332
See application file for complete search history.

(56) References Cited

U.S. PATENT DOCUMENTS 6,087,148 A    7/2000    Rancke-Madsen et al. . 435/209

FOREIGN PATENT DOCUMENTS

| JP | 05-146279 | 6/1993 |
|----|-----------|--------|
| JP | 06-056884 | 3/1994 |
| JP | 07-177896 | 7/1995 |
| WO | WO 93/25573 | 12/1993 |
| WO | WO 97/349919 | 9/1997 |

OTHER PUBLICATIONS

C. Jelsch and C. Didierjean. Acta Cryst (1999) c55, 1538-1540.*
A. McPherson. Eur. J. Biochem. (1990), 189, pp. 1-23.*
Protein purification -http://www.biotech.vt.edu/classes/bion_4784/9-ProteinPurification/ProteinPurification.html, 4 pages, Oct. 21, 2000; accessed Jun. 14, 2005.*

* cited by examiner

*Primary Examiner*—Bruce R. Campell
*Assistant Examiner*—Andrew D. Kosar
(74) *Attorney, Agent, or Firm*—Fitzpatrick, Cella, Harper & Scinto

(57) ABSTRACT

The present invention provides crystals of glutathione oxidized n hydrate (wherein n is an integer or a fraction of not less than 0 and less than 8) useful, for example, as final products of, as raw materials for, or as intermediates of health foods, pharmaceuticals, cosmetics or the like, and a process for producing crystals of glutathione oxidized, which comprises a step of crystallizing glutathione oxidized from a mixture of an aqueous solution containing glutathione oxidized and a water-miscible organic solvent and which is suitable for large-scale synthesis or industrialization.

9 Claims, No Drawings

US 7,094,870 B2

CRYSTALS OF OXIDIZED GLUTATHIONE AND PROCESS FOR PRODUCING THE SAME

TECHNICAL FIELD

The present invention relates to crystals of glutathione oxidized which are useful, for example, as final products of, as raw materials for, or as intermediates of health foods, pharmaceuticals, cosmetics or the like, and a process for producing crystals of glutathione oxidized.

BACKGROUND ART

Oxidized glutathione has an effect similar to that of glutathione reduced. As the effect that glutathione oxidized has, an effect such as detoxification in the liver by orally administration is known [J. Nutr. Sci. Vitaminol., Vol. 44, p. 613 (1998)]. Thus, glutathione oxidized can be used for various purposes for which glutathione reduced is used, and is, for example, useful as final products of, as raw materials for, or as intermediates of health foods, pharmaceuticals, cosmetics or the like.

As a process for producing glutathione oxidized, processes, such as a process for preparing a yeast extract thereof by concentration, dilution or the like of a glutathione oxidized solution which is obtained by oxidizing an aqueous solution, a yeast solution or the like of glutathione reduced obtained by a fermentation, an enzymatic preparation or the like, as a raw material, according to Japanese Published Unexamined Patent Application No. 146279/93, 177896/95 or the like; a process for preparing powders of a yeast extract containing glutathione oxidized by adding vehicles to the glutathione oxidized solution, and freeze-drying, spray-drying or the like; and a process for preparing powders (amorphous) of glutathione oxidized by separating and purifying the glutathione oxidized solution, and freeze-drying, spray-drying or the like, are known.

Since glutathione oxidized is difficult to obtain as crystals, glutathione oxidized in a solid form is supplied in the form of powders obtained by freeze-drying or the like (freeze-dried powders; amorphous). However, the freeze-drying is not suitable for industrial large-scale supply in its productivity. Accordingly, there exists a demand for crystals of glutathione oxidized and a process for production thereof which are suitable for large-scale supply or industrialization.

Furthermore, the freeze-dried powders of glutathione oxidized are known to have a problem in respect of stability because of their hygroscopicity, deliquescence, etc. Thus, they need to be refrigerated or frozen, or require special packaging to avoid moisture absorption when, for example, stored, transported or distributed. Accordingly, for its industrial large-scale supply, crystals of glutathione oxidized that can be stored at ordinary temperature and a process for production thereof are required.

DISCLOSURE OF INVENTION

An object of the present invention is to provide crystals of glutathione oxidized useful, for example, as final products of, as raw materials for, or as intermediates of health foods, pharmaceuticals, cosmetics or the like, and to provide a process for producing crystals of glutathione oxidized which is suitable for large-scale synthesis or industrialization.

The present invention relates to the following (1) to (12):

(1) A crystal of a glutathione oxidized n hydrate (wherein n is an integer or a fraction of not less than 0 and less than 8).

(2) The crystal of a glutathione oxidized n hydrate according to the above (1), wherein n is an integer or a fraction of 0 to 2.

(3) A crystal of a glutathione oxidized monohydrate.

(4) A process for producing crystals of glutathione oxidized which comprises a step of crystallizing glutathione oxidized from a mixture of an aqueous solution containing glutathione oxidized and a water-miscible organic solvent.

(5) A process for producing crystals of glutathione oxidized which comprises a step of adding or dropping a water-miscible organic solvent to an aqueous solution containing glutathione oxidized.

(6) A process for producing crystals of glutathione oxidized which comprises a step of adding or dropping an aqueous solution containing glutathione oxidized to a water-miscible organic solvent.

(7) The process according to any one of the above (4) to (6), wherein the crystals of glutathione oxidized are crystals of a glutathione oxidized n hydrate (wherein n is an integer or a fraction of not less than 0 and less than 8).

(8) The process according to the above (7), wherein n is an integer or a fraction of 0 to 2.

(9) The process according to the above (7), wherein n is 1.

(10) The process according to any one of the above (4) to (9), wherein the water-miscible organic solvent is an alcohol or a ketone.

(11) The process according to any one of the above (4) to (9), wherein the water-miscible organic solvent is methanol or acetone.

(12) The process according to any one of the above (4) to (11), wherein the aqueous solution containing glutathione oxidized is an aqueous solution prepared by treating a glutathione oxidized solution with a synthetic adsorbent resin or an ion-exchange resin.

In the present invention:

(i) The crystal(s) of glutathione oxidized is/are not particularly limited, but is/are preferably crystal(s) of a glutathione oxidized n hydrate (wherein n is as defined above), and more preferably the crystal(s) of a glutathione oxidized n hydrate wherein n is an integer or a fraction of 0 to 2.

(ii) The glutathione oxidized solution may be any solution containing glutathione oxidized. Examples of the glutathione oxidized solution include a reaction solution, a culture solution, a yeast solution, and a cell-free culture solution of glutathione oxidized which is prepared by oxidizing glutathione reduced with oxygen, hydrogen peroxide, an enzyme to oxidize ascorbic acid or the like in a manner similar to that described in Japanese Published Unexamined Patent Application No. 146279/93, 177896/95 or the like, wherein the glutathione reduced may be prepared as a reaction solution containing glutathione reduced, or as a purified solution thereof or freeze-dried powders thereof by synthesis, fermentation, yeast fermentation or the like, in a manner similar to that described in Japanese Published Examined Patent Application No. 239/69, 4755/71, 2838/71, Japanese Published Unexamined Patent Application No. 74595/86 or the like.

(iii) The aqueous solution containing glutathione oxidized may be any aqueous solution containing glutathione oxidized, but the purity of glutathione oxidized is preferably 50% or more, more preferably 70% or more of components that are dissolved in the aqueous solution. The aqueous solution may also contain an organic solvent, for example, an alcohol such as methanol, ethanol, isopropyl alcohol, or n-propanol; a ketone such as acetone or methyl ethyl ketone; or the like. Preferably, the water content of the aqueous solution is 20% or more. Specific examples of the aqueous solution containing glutathione oxidized include those prepared by subjecting the glutathione oxidized solution, which is the same as the glutathione oxidized solution described above, to pretreatment. Examples of the pretreatment include treatment with a membrane, gel filtration, treatment with activated carbon, treatment with an ion-exchange resin, treatment with a synthetic adsorbent resin, treatment with a chelate resin, solvent precipitation, etc. Preferred examples of the pretreatment are treatment with activated carbon, treatment with an ion-exchange resin, treatment with a synthetic adsorbent resin, solvent precipitation, etc. Among them, treatment with a synthetic adsorbent resin or treatment with an ion-exchange resin is more preferable. These treatments may also be appropriately employed in combination.

Furthermore, in the aqueous solution containing glutathione oxidized, the concentration of glutathione oxidized is preferably 50–700 g/L, more preferably 100–400 g/L, and the solution is appropriately prepared by concentration or the like.

(iv) The water-miscible organic solvent may be any organic solvent that is miscible with water. Preferred are, for example, alcohols such as methanol, ethanol, isopropyl alcohol and n-propanol; and ketones such as acetone and methyl ethyl ketone.

(v) Examples of the synthetic adsorbent resin include nonpolar porous adsorbent resins, specifically DIAION™ HP series (e.g., HP10, HP20, HP21, HP30, HP40 and HP50; Mitsubishi Chemical Corporation), DIAION™ SP800 series (e.g., SP800, SP825, SP850 and SP875; Mitsubishi Chemical Corporation), DIAION™ SP200 series (e.g., SP205, SP206, SP207 and SP207SS; Mitsubishi Chemical Corporation), and AMBERLITE™ XAD series (e.g., XAD4, XAD7HP, XAD16 and XAD1600; Rohm and Haas Company), etc. Among them, SP207 is preferred.

(vi) Examples of the ion-exchange resin include strong base anion exchange resins, weak base anion exchange resins, strong acid cation exchange resins, and weak acid cation exchange resins.

Examples of the strong base anion exchange resin include DIAION™ PA series (e.g., PA306, PA312 and PA412; Mitsubishi Chemical Corporation). Examples of the weak base anion exchange resin include DIAION™ WA series (e.g., WA10, WA20 and WA30; Mitsubishi Chemical Corporation).

Examples of the strong acid cation exchange resin include AMBERLITE™ IR series (e.g., 124Na and 252Na; Organo Corporation), DOWEX™ (e.g., XUS-40232.01; Dow Chemical Company). Examples of the weak acid cation exchange resin include AMBERLITE™ IRC series (e.g., IRC-50 and IRC-70; Rohm and Haas Company).

One example of the process for producing the crystals of glutathione oxidized is described in detail below.

Production Process:

1. Preparation of an Aqueous Solution Containing Glutathione Oxidized

In accordance with the process described in Japanese Published Unexamined Patent Application No. 146279/93, 177896/95 or the like, glutathione reduced is oxidized by, oxygen, hydrogen peroxide, an enzyme to oxidize ascorbic acid or the like to obtain a reaction solution, a culture solution, a yeast solution or a cell-free culture solution containing glutathione oxidized. The resulting solution is appropriately pretreated to adjust the purity of glutathione oxidized, to for example, 50% or more, preferably 70% or more of components that are dissolved in the solution. The pretreated or untreated solution is concentrated to, for example, 50–700 g/L, preferably 100–400 g/L of the glutathione oxidized to obtain an aqueous solution containing glutathione oxidized. Alternatively, powders of the pretreated or untreated solution can be prepared by freeze-drying and then the resulting powders are dissolved in water at the same concentration to obtain the aqueous solution containing glutathione oxidized. In this case, commercially available glutathione oxidized powders may also be used.

The pretreatment to prepare the aqueous solution containing glutathione oxidized includes treatment with a membrane, gel filtration, and preferably includes treatment with activated carbon, treatment with an ion-exchange resin, treatment with a synthetic adsorbent resin, treatment with a chelate resin (examples of the chelate resin include DUO-LITE™ C467 manufactured by Sumitomo Chemical Co., Ltd.), solvent precipitation, etc. Among them, treatment with a synthetic adsorbent resin or treatment with an ion-exchange resin is more preferable. These treatments may also be used in combination.

More specifically, an aqueous solution containing high-purity glutathione oxidized may be prepared by separation and purification in which the reaction solution, the culture solution, the yeast solution, the cell-free culture solution or the like of glutathione oxidized is passed through a synthetic adsorbent resin, preferably SP207, using, as an eluate, water or a water-miscible organic solvent (the water-miscible organic solvent is same as described above) alone or in combination of two or more. Alternatively, it may be prepared by separation and purification in which the reaction solution, the culture solution, the yeast solution, the cell-free culture solution or the like of glutathione oxidized is passed through a strong acid cation exchange resin ($H^+$ type) with a degree of cross-linking not less than 12%, preferably SK112 or SK116, and then through a strong acid cation exchange resin ($H^+$ type) with a degree of cross-linking not more than 4%, preferably SK102 or XUS-40232.01, both using, as an eluate, water or the water-miscible organic solvent (the water-miscible organic solvent is same as described above) alone or in combination of two or more; an aqueous ammonia solution; an aqueous sodium chloride solution; or the like. The glutathione reduced which is a raw material may be commercially available, or a reaction solution containing glutathione reduced, which was prepared by synthesis, fermentation, or a yeast fermentation in accordance with a conventional method (as described in Japanese Published Examined Patent Application No. 239/69, 4755/71, 46-2838/71, Japanese Published Unexamined Patent Application No. 61-74595 or the like), a purified solution thereof or freeze-dried powders thereof.

2. Production of Crystals of Glutathione Oxidized

The pH value of the aqueous solution containing glutathione oxidized, which is prepared in 1, may be, if necessary, adjusted to, for example, 2.5–3.5 with hydrochloric acid or sulfuric acid, or an aqueous solution of sodium hydroxide, etc., and then the resulting solution is crystallized while adding a water-miscible organic solvent thereto for 1 minute to 10 hours, preferably 1 hour to 7 hours at a temperature between −20° C. and the boiling point of the water-miscible organic solvent or under reflux condition. After the addition is completed, the resulting solution is further stirred and crystallized for another 15 minutes to 20 hours, preferably 0.5 hours to 6 hours at a temperature between −20° C. and 35° C. to precipitate crystals. The precipitated crystals are separated by centrifugal filtration, decantation or the like. The isolated crystals are washed with water or a water-miscible organic solvent, and then dried under reduced pressure or by airflow to obtain crystals of glutathione oxidized. Furthermore, the crystals of glutathione oxidized may be further purified by carrying out procedures such as washing, drying and recrystallization.

Alternatively, the pH value of the aqueous solution containing glutathione oxidized, which is prepared in 1, may be also, if necessary, adjusted to, for example, 2.5–3.5 with hydrochloric acid or sulfuric acid, or an aqueous solution of sodium hydroxide, etc., and then the resulting solution is crystallized while adding that into a water-miscible organic solvent to obtain crystals of glutathione oxidized.

In large-scale synthesis or industrialization, the two processes described above are more preferred, but the pH value of the aqueous solution containing glutathione oxidized, which is prepared in 1, may be also, if necessary, adjusted to, for example, 2.5–3.5 with hydrochloric acid or sulfuric acid, or an aqueous solution of sodium hydroxide, etc., and then the resulting solution is crystallized by leaving it standing for 24 hours or more to obtain crystals of glutathione oxidized.

Seed crystals may be added thereto in the crystallization, if necessary.

The crystals of glutathione oxidized obtained by the above-described processes may be obtained as adducts with various water-miscible organic solvents. Such adducts are also included in the crystals of the present application.

Furthermore, the crystals of glutathione oxidized obtained by the above-described processes sometimes exist in different crystalline forms or different particle sizes, and these may be obtained alone or as a mixture. Such different crystalline forms or different particle sizes, which are obtained alone or as a mixture, are also included in the crystals of the present application.

The storage stability (hygroscopicity) of the crystals of glutathione oxidized of the present invention is illustrated in the following test example.

Test Example: Comparison of hygroscopicity of Crystals of Glutathione Oxidized Monohydrate and Freeze-dried Glutathione Oxidized Powders Crystals of Glutathione Oxidized Monohydrate obtained in Example 3 and Freeze-dried Glutathione Oxidized Powders obtained in Reference Example 1 were examined for their hygroscopicity under the condition of normal pressure at 23° C. and a humidity of 70%. As a result, Freeze-dried Glutathione Oxidized Powders obtained in Reference Example 1 absorbed a significant amount of moisture and deliquesced in two days. In contrast, Crystals of Glutathione Oxidized Monohydrate obtained in Example 3 showed little change in water content and was very stable.

The present invention is described in detail below in Examples and Reference Example, but neither of them should be construed to limit the present invention.

BEST MODES FOR CARRYING OUT THE INVENTION

EXAMPLE 1

Production of Crystals of Glutathione Oxidized (Seed Crystals)

Freeze-dried Glutathione Oxidized Powders (3.0 g) obtained in Reference Example 1 was dissolved in water to prepare an aqueous solution containing glutathione oxidized (5 mL, the concentration of glutathione oxidized: 600 g/L). The resulting aqueous solution was left to standing for 48 hours for crystallization. The resulting crystals were separated by filtration and dried in airflow to obtain Crystals of Glutathione Oxidized Monohydrate (0.6 g).

Melting point: 191° C.

Water content (Karl Fischer titration method): 3.08%

Powder x-ray diffraction [the angle of diffraction ($2\theta°$); values in parentheses indicate intensity ratios ($I/I_0$)]: 5.60 (116), 7.25(130), 10.70(87), 11.20(80), 11.75(70), 12.70 (106), 14.3(271), 14.6(326), 15.75(96), 16.10(123), 16.85 (130), 18.35(565), 18.85(925), 19.45(652), 19.75(379), 20.50(452), 20.75(375), 21.35(1090), 22.10(291), 23.20(293), 23.50(314), 24.15(241), 24.80(303), 25.70(248), 26.25(155), 27.10(235), 27.55(181), 28.20(208), 28.55(239), 29.00(354), 29.85(157), 30.25(163), 30.85(130), 31.40(145), 32.00(155), 33.10(150), 34.15(173), 35.65(227), 35.95(194), 36.70(178), 37.00(173), 38.50(161), 39.00(150), 39.50(120), 40.65(163), 41.20(132)

EXAMPLE 2

Production 1 of Crystals of Glutathione Oxidized

Freeze-dried Glutathione Oxidized Powders (10.0 g) obtained in Reference Example 1 was dissolved in water to prepare an aqueous solution containing glutathione oxidized (33 mL, the concentration of glutathione oxidized: 300 g/L). The resulting aqueous solution was heated to 50° C., and the crystals (0.1 g) obtained in Example 1 were added thereto as seed crystals. Methanol (66 mL) was added to the resulting solution over 5 hours for crystallization. After the, crystallized solution was cooled, to 20° C. over 30 minutes, the crystals were separated by filtration and dried by airflow to obtain Crystals of Glutathione Oxidized Monohydrate (8.5 g).

EXAMPLE 3

Production 2 of Crystals of Glutathione Oxidized

The pH value of a reaction solution of glutathione reduced, which was prepared in accordance with a method described in Example 2 of Japanese Published Unexamined Patent Application No. 74595/86, was adjusted to 7.5 with an aqueous solution of sodium hydroxide in accordance with a process described in Japanese Published Unexamined Patent Application Publication No. 146279/93. After the resulting solution was oxidized by blowing oxygen thereto to obtain a reaction solution of glutathione oxidized (48.1 L, the concentration of glutathione oxidized: 18.0 g/L). The pH value of the resulting reaction solution was adjusted to 3.0 with sulfuric acid, and then a cell-free culture solution of glutathione oxidized obtained by removing cells (55.5 L, the concentration of glutathione oxidized: 14.4 g/L). After the cell-free culture solution was passed through DIAION™ SK116 (22 L), and the resulting solution was adsorbed on DOWEX™ XUS-40232.01 (13 L) and was eluted by ammonia water (20 L, concentration: 2 mol/L). The eluate was passed through DIAION™ SK116 (7 L) for ion exchange and removal of ammonia to obtain an aqueous solution containing glutathione oxidized (19 L, the concentration of glutathione oxidized: 35.4 g/L). After activated charcoal powders (130 g) was added to the solution, and the solution was stirred at 40° C. for 1 hour and was filtered to remove the activated charcoal powders. The resulting filtrate was concentrated to 2.24 L (the concentration of glutathione oxidized: 300 g/L). The crystals (13 g) prepared in accordance with the process described in Example 1 were added thereto as seed crystals while stirring at 35° C. Methanol (4.6 L) was added to the solution over 5 hours for crystallization. After the crystallized solution was cooled to 20° C. over 2 hours, the crystals were separated by filtration and dried by airflow to obtain Crystals of Glutathione Oxidized Monohydrate (610 g).

REFERENCE EXAMPLE 1

Production of Freeze-dried Glutathione Oxidized Powders

In accordance with a process described in Japanese Published Unexamined Patent Application No. 146279/93, 4.8 g of glutathione reduced was dissolved in water (24 mL). The pH value of the resulting aqueous solution was adjusted to 7.5 with an aqueous solution of sodium hydroxide and then was stirred in the presence of copper sulfate. The reaction solution was passed through DIAION™ SK116 (32 mL) and DUOLITE™ C467 (4 mL, Sumitomo Chemical Co., Ltd.). The treated solution was concentrated to obtain an aqueous solution containing glutathione oxidized (11 mL, the concentration of glutathione oxidized: 300 g/L). The aqueous solution was freeze-dried to obtain 3.0 g of Freeze-dried Glutathione Oxidized Powders.

The invention claimed is:

1. An isolated crystal of a glutathione oxidized monohydrate.

2. A process for producing isolated and dried crystals of glutathione oxidized monohydrate which comprises a step of crystallizing glutathione oxidized from a mixture of an aqueous solution containing glutathione oxidized and a water-miscible organic solvent by stirring the mixture.

3. A process for producing isolated and dried crystals of glutathione oxidized monohydrate which comprises a step of crystallizing glutothione oxidized monohydrate by adding or dropping a water-miscible organic solvent to an aqueous solution containing glutathione oxidized, and stirring the resulting mixture.

4. A process for producing isolated and dried crystals of glutathione oxidized monohydrate which comprises a step of crystallizing glutothione oxidized monohydrate by adding or dropping an aqueous solution containing glutathione oxidized to a water-miscible organic solvent, and stirring the resulting mixture.

5. The process according to any one of claims 2 to 4, wherein the water-miscible organic solvent is an alcohol or a ketone.

6. The process according to any one of claims 2 to 4, wherein the water-miscible organic solvent is methanol or acetone.

7. The process according to any one of claims 2 to 4, wherein the aqueous solution containing glutathione oxidized is an aqueous solution prepared by treating a glutathione oxidized solution with a synthetic adsorbent resin or an ion-exchange resin.

8. The process according to claim 7, wherein the water-miscible organic solvent is an alcohol or a ketone.

9. The process according to claim 7, wherein the water-miscible organic solvent is methanol or acetone.

* * * * *